| United States Patent [19] | [11] Patent Number: 4,849,452 |
|---|---|
| Dulce et al. | [45] Date of Patent: Jul. 18, 1989 |

[54] NEPHRO-UROLOGICAL MEDICAMENT

[75] Inventors: Hans-Joachim Dulce, Berlin; Werner Stumpf, Bergisch Gladbach, both of Fed. Rep. of Germany

[73] Assignee: Dr. Madaus & Co., Cologne, Fed. Rep. of Germany

[21] Appl. No.: 808,014

[22] Filed: Dec. 11, 1985

[30] Foreign Application Priority Data

Dec. 12, 1984 [DE] Fed. Rep. of Germany ....... 3445253

[51] Int. Cl.⁴ ............................................ A61K 31/195
[52] U.S. Cl. ..................................... 514/562; 514/891
[58] Field of Search ................................ 514/891, 562

[56] References Cited

U.S. PATENT DOCUMENTS 4,499,107 12/1985 Bergamaschi et al. ............. 514/575

FOREIGN PATENT DOCUMENTS 3445253 6/1986 Fed. Rep. of Germany ...... 514/562

*Primary Examiner*—Douglas W. Robinson
*Assistant Examiner*—Richard M. Kearse
*Attorney, Agent, or Firm*—Felfe & Lynch

[57] ABSTRACT

A method of treating nephro-urological disorders, such as kidney stones, phosphate renal calculi formulation, infections connected with urease formation, and abnormal calcium or phosphate excretion is disclosed. The method comprises administration of L-cysteine, or its acid addition salts, in effective amounts to patients suffering from said disorders. In addition, compositions containing the effective compounds are disclosed.

12 Claims, No Drawings

NEPHRO-UROLOGICAL MEDICAMENT

BACKGROUND OF THE INVENTION

The subject matter of the invention is a nephro-urological medicament which is especially suitable for combatting phosphate renal calculi.

In epidemiological studies of recent years it has been shown that an average of 4% of the adult population suffers once or more often in the course of life from renal calculi (kidneystones). Renal calculi are borderline cases of biomineralization. They are caused by a number of pathologicoanatomic, metabolical and physiochemical factors. The causes of renal calculi formation also determine their composition. By physiochemical methods of examination, such as infrared spectroscopy and X-ray diffraction, it is possible to perform a precise, quantitative analysis of renal calculi.

A large amount—about 15 to 20%—of the renal calculus consists of various phosphates. A summary of the phosphates most frequently occurring in the renal calculus is given below.

Chemical names, chemical formula, and mineralogical names of the most important phosphate kidneystones:

| Chemical name | Formula | Mineralogical name |
|---|---|---|
| Calcium hydrogen phosphate | $CaHPO_4 2H_2O$ | Brushite |
| Tricalcium phosphate | $Ca_3(PO_4)_2$ | Whitlockite |
| Hydroxycalcium phosphate | $Ca_{10}(PO_4)_6(OH)_2$ | Hydroxylapatite |
| Carbonate apatite | $Ca_{10}(PO_4CO_3OH)_6(OH)_2$ | Dahllite |
| Magnesium ammonium phosphate | $MgNH_4PO_4.6H_2O$ | Struvite |

A deciding factor in the formation of phosphate calculi is the pH of the urine. The overwhelming number of phosphate calculi form in an alkaline environment. Apatite, carbonate apatite and struvite crystallize, for example, at urine pH levels above 7.0. Brushite, however, crystallizes at urine pH levels of 6.8 to 7.0.

The formation of phosphate renal calculi is based on a variety of causes. Some causes are urinary infections by germs producing urease, which alkalinize the urine by the cleavage of urea; the result is a supersaturation of magnesium ammonium phosphate, calcium phosphate and monoammonium urate in the urine, followed by crystalluria and the subsequent formation of kidneystones like the above-named: struvite, carbonate apatite and monoammonium urate. In this development, aggravating factors are normally present, such as an excessively low urine volume, a deficiency of citrate or inhibitors, and an excessively high concentration of calcium and phosphate in the urine.

Another cause of the formation of calcium phosphate concretions is metabolical disturbances, such as renal tubulary acidosis, which likewise leads to an elevation of the pH in the urine; the incomplete form of renal tubulary acidosis can be compensated by acidification of the urine.

Furthermore, in addition to the altered calcium and phosphate excretion, e.g., under the conditions of primary hyperparathyroidism, the urine pH is an aggravating factor in the formation of phosphate stones. Accordingly, a lowering of the pH may here again be necessary.

The therapeutic object in cases of phosphate stone diathesis, namely the acidification of the urine, should always be accomplished with the lowest possible burden on the metabolism. Consequently, those medicaments are to be favored which in low dosage produce a high acidifying action.

To combat phosphate calculi, L-methionone, $NH_4Cl$, acidolpepsin, and ascorbic acid have been used as urinary acidifying agents. In some cases, very high daily doses of these drugs must be applied if a sufficient urinary acidification is to be achieved. Also due to the necessary high absorption, however, the organism is at the same time subjected to a high metabolical stress. This is true especially of the liver metabolism, and can lead to alteration of the blood and urine analysis.

The object of the invention was therefore a preparation for urinary acidification which can be administered in sufficient quantity without excessive stress on the organism, especially on the liver metabolism.

THE INVENTION

The nephro-urological substance developed according to the invention for this purpose is characterized by a content of L-cysteine and/or pharmacologically compatible acid addition salts of L-cysteine. Preferred are dosage units with a content of 0.75 g of L-cysteine monohydrate monohydrochloride. In comparison to the known L-methionine, which is employed in daily doses of 3 grams per diem for an acidification of the urine (corresponding to 40.2 mmol $H^+$), as little as 2.35 grams per diem of L-cysteine-$HCl.H_2O$ will suffice for the same effect. The following Table I shows the amounts of L-cysteine-$HCl.H_2O$ and L-methionine necessary for the same acidification.

TABLE 1

| mmol $H^+$ | L—cysteine-$HCl.H_2O$ | L—methionine/day |
|---|---|---|
| 25 | 1.464 g | 1.865 g |
| 35 | 2.049 g | 2.611 g |
| 40 | 2.342 g | 2.984 g |
| 48 | 2.810 g | 3.581 g |

As it can be seen, the necessary L-methionine dosage is definitely higher.

The compound L-methionine, which is also used for the acidification of the urine, has an —$SCH_3$ group instead of an —SH group as in L-cysteine. In the metabolization, therefore, the two compounds go different ways. The necessary demethylation of L-methionine, before —S— is oxidized in the body to $SO_4^=$, entails a stress on the organism and the formation of intermediates.

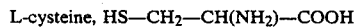
L-cysteine, HS—$CH_2$—CH($NH_2$)—COOH

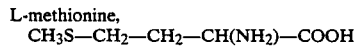
L-methionine, $CH_3$S—$CH_2$—$CH_2$—CH($NH_2$)—COOH

Instead of the cysteine hydrochloride, other acid addition salts can, of course, be provided, or the L-cysteine itself, which then is converted in the stomach to cysteine hydrochloride. For reasons of $H^+$ balancing in the urine, however, L-cysteine hydrochloride is preferred.

In different experimental series, groups of 6 healthy male subjects with an average body weight of 75 kilograms and ages of 25 to 30 years were treated in the following manner:

The subjects received a normal, roughly standardized, mixed diet. After a control period of 4 days, acid supplying agents were administered to the subjects for 14 days at mealtimes, in the following daily amounts:

Group A: 3×2 tablets of acid mixture (one tablet=150 mg of $NH_4Cl$, 100 mg lysine-HCl, 100 mg betaine-HCl) corresponding to 24 mmol of $H^+$ ions;

Group B: 3×4 tablets of acid mixture (see above corresponding to 48 mmol of $H^+$ ions;

Group C: 2.4 g of cysteine-$HCl.H_2O$ corresponding to 41 mmol of $H^+$ ions and 13.7 mmol of sulfate.

Before the midday meal, about 22 ml of whole blood was taken from the subjects daily during the control period and on the 2nd, 4th, 8th, 11th and 14th day during the test period. 2 ml of the blood sample was treated with heparin for the blood gas analysis, and the remaining 20 ml of blood was evaluted in the form of centrifuged serum without additive for the determination of sodium, potassium, chloride, calcium, inorganic phosphate, parathyroid hormone, 25-OH-vitamin $D_3$, ammonia, creatinine, uric acid, sulfate, magnesium, gamma-GT and citrate.

Throughout the test period, the 24 hour urine was collected and kept refrigerated with 5 ml of isopropanol as preservative. The collecting period began at 7:00 AM and ended the next morning at the same time.

The 24-hour urine was tested for volume, specific gravity, pH, ammonia, titration acidity, total acidity, $pCO_2$, potassium, sodium, chloride, calcium, inorganic phosphate, magnesium, sulfate, creatinine, uric acid, oxalate, citrate and cyclic AMP.

The following Tables II to IV show the results obtained with cysteine-HCl, together with data from a retesting.

TABLE II

Effect of 2.4 g of cysteine-HCl (41 mmol acid) per day on the serum parameters of 6 healthly human subjects

| | Control days | Cysteine-HCl dosage (41 mmol $H^+$/d) | | |
|---|---|---|---|---|
| Serum parameter | Days 1-4 | Days 2-7 | Days 8-14 | Days 2-14 |
| pH | 7.35 ± 0.01 | 7.30 ± 0.03 | 7.35 ± 0.02 | 7.33 ± 0.04 |
| Std. $HCO_3^-$ (mmol/l) | 23.6 ± 0.1 | 22.7 ± 3.8 | 23.6 ± 0.5 | 23.2 ± 2.3 |
| $pCO_2$ (kPa) | 6.9 ± 0.4 | 7.0 ± 0.5 | 6.6 ± 0.3 | 6.7 ± 0.4 |
| $NH_4^+$ (mcmol/l) | 23 ± 3 | 26 ± 5 | 22 ± 4 | 24 ± 4 |
| K (mmol/l) | 4.6 ± 0.1 | 4.4 ± 0.1 | 4.3 ± 0.1 | 4.4 ± 0.1 |
| Na (mmol/l) | 141 ± 1 | 138 ± 2 | 140 ± 1 | 139 ± 2 |
| $SO_4^-$ (mcmol/l) | 175 ± 29 | 228 ± 6 | 208 ± 18 | 216 ± 17 |
| Cl (mmol/l) | 98 ± 1 | 98 ± 1 | 97 ± 1 | 98 ± 1 |
| Uric acid (mcmol/l) | 363 ± 12 | 358 ± 19 | 355 ± 24 | 356 ± 20 |
| $PO_4^-$ (mmol/l) | 1.22 ± 0.04 | 1.21 ± 0.10 | 1.27 ± 0.05 | 1.24 ± 0.07 |
| Ca (mmol/l) | 2.47 ± 0.11 | 2.45 ± 0.12 | 2.48 ± 0.6 | 2.47 ± 0.08 |
| Parathyroid hormone | 428 ± 30 | 390 ± 3 | 388 ± 17 | 389 ± 22 |
| 25-OH vit. $D_3$ (nmol/l) | 92 ± 5 | 85 ± 3 | 90 ± 5 | 87 ± 5 |
| gamma-GT (U/l) | 10 ± 1 | 10 ± 1 | 10 ± 1 | 10 ± 1 |
| K. clearance (ml/min) | 128 ± 2 | 142 ± 2 | 143 ± 16 | 143 ± 12 |
| Creatinine (mcmol/l) | 92 ± 2 | 91 ± 2 | 86 ± 6 | 89 ± 5 |

TABLE III

Effect of 2.4 g of cysteine-HCl (41 mmol acid) per day on the urine parameters of 6 healthy human subjects

| | Control days | | | |
|---|---|---|---|---|
| Urine parameter | Days 1-4 | Day 1 | Days 2-7 | Days 8-14 |
| pH | 6.25 ± 0.21 | 5.67 | 5.56 ± 0.07 | 5.66 ± 0.09 |
| $HCO_3^-$ (mmol/d) | 4.1 ± 1.9 | 0.8 | 0.5 ± 0.1 | 0.8 ± 0.3 |
| $pCO_2$ (kPa) | 7.3 ± 1.2 | 5.4 | 4.6 ± 0.5 | 5.5 ± 0.8 |
| $NH_4^+$ (mmol/d) | 34.7 ± 2.3 | 50.0 | 63.4 ± 5.5 | 69.6 ± 3.5 |
| Titr. acidity (mmol/d) | 29.8 ± 3.3 | 41.0 | 48.9 ± 4.6 | 45.8 ± 4.3 |
| Total acidity (mmol/d) | 60.1 ± 5.2 | 90.2 | 111.6 ± 9.6 | 112.3 ± 8.3 |
| K (mmol/d) | 80 ± 6 | 86 | 74 ± 5 | 76 ± 5 |
| Na (mmol/d) | 197 ± 26 | 202 | 204 ± 29 | 203 ± 22 |
| $SO_4^-$ (mmol/d) | 24.6 ± 1.0 | 34.7 | 38.2 ± 1.5 | 38.7 ± 2.3 |
| Cl (mmol/d) | 177 ± 32 | 200 | 197 ± 29 | 204 ± 18 |
| Uric acid (mmol/d) | 5.41 ± 0.24 | 4.36 | 5.28 ± 0.38 | 5.45 ± 0.41 |
| $PO_4^-$ (mmol/d) | 34.7 ± 3.1 | 31.7 | 40.2 ± 3.4 | 35.9 ± 5.1 |
| Oxalate (mcmol/d) | 157 ± 30 | 208 | 192 ± 41 | 168 ± 14 |
| Mg (mmol/d) | 5.18 ± 0.48 | 4.98 | 5.69 ± 0.33 | 5.61 ± 0.39 |
| Ca (mmol/d) | 4.68 ± 1.49 | 7.19 | 7.19 ± 1.84 | 4.79 ± 0.38 |
| cAMP (mcmol/d) | 5.1 ± 0.21 | 4.2 | 5.4 ± 0.36 | 5.2 ± 0.36 |
| Volume (ml/d) | 1579 ± 205 | 1700 | 1631 ± 188 | 1617 ± 168 |
| Spec. Gr. (g/l) | 1020 ± 1 | 1017 | 1018 ± 3 | 1019 ± 2 |
| Creatinine (nmol/d) | 17.0 ± 0.4 | 18.2 | 18.3 ± 0.6 | 17.8 ± 0.8 |

TABLE IV

Effect of 2.4 g of cysteine-HCl (41 mmol acid) per day on the urine parameters of 6 healthy human subjects

| Urine parameter | Cysteine-HCl Days 2-14 | Follow-up testing Day 1 | Follow-up testing Days 2-3 |
|---|---|---|---|
| pH | 5.61 ± 0.10 | 5.66 | 6.20 ± 0.06 |
| $HCO_3^-$ (mmol/d) | 0.6 ± 0.3 0.6 | 3.7 ± 0.9 | |
| $pCO_2$ (kPa) | 5.1 ± 0.8 | 5.4 | 7.5 ± 0.3 |
| $NH_4^+$ (mmol/d) | 66.7 ± 5.4 | 60.0 | 49.0 ± 4.5 |
| Titr. acidity (mmol/d) | 47.9 ± 4.6 | 43.0 | 32.9 ± 7.6 |
| Total acidity (mmol/d) | 112.0 ± 8.6 | 102.2 | 79.2 ± 11.7 |
| K (mmol/d) | 75 ± 5 | 68 | 65 ± 2 |
| Na (mmol/d) | 203 ± 24 | 170 | 196 ± 23 |
| $SO_4^-$ (mmol/d) | 38.5 ± 1.9 | 26.0 | 25.5 ± 4.3 |
| Cl (mmol/d) | 201 ± 23 | 179 | 196 ± 6 |
| Uric acid (mmol/d) | 5.37 ± 0.39 | 4.67 | 5.17 ± 0.42 |
| $PO_4^-$ (mmol/d) | 37.9 ± 4.8 | 37.2 | 36.5 ± 4.9 |
| Citrate (mmol/d) | 1.82 ± 0.25 | 1.62 | 2.09 ± 0.49 |
| Oxalate (mcmol/d) | 180 ± 32 | 138 | 157 ± 20 |
| Mg (mmol/d) | 5.65 ± 0.35 | 4.82 | 5.05 ± 0.14 |
| Ca (mmol/d) | 5.90 ± 1.74 | 4.99 | 5.02 ± 0.27 |
| cAMP (mcmol/d) | 5.3 ± 0.36 | 4.8 | 4.6 ± 0.57 |
| Volume (ml/d) | 1624 ± 167 | 1470 | 1692 ± 153 |
| Spec. Gr. (g/l) | 1019 ± 2 | 1020 | 1018 ± 2 |
| Creatinine (nmol/d) | 18.0 ± 0.8 | 17.7 | 17.9 ± 1.2 |

The tabulated data give the following picture:

A daily acid dose of 41 mmol as cysteine-HCl (approximately 13.7 nmol Cl+S) leads to urinary acidosis with elevated sulfate excretion and only a brief rise in the calcium transformation without any increase in the parathyroid hormone secretion.

Acid-Base transformation

The urinary pH decreases during the acid treatment by an average of 0.64 pH units to pH 5.61.

The total acidity of the urine ($NH_4^+$ + tit.acid. − $HCO_3^-$) increases by an average of 51.9 mmol/d from 60.1 to 112.0 mmol/d, while the titration acidity increases by 18.1 mmol/d and the ammonia excretion by 32.0 mmol/d, and the bicarbonate excretion decreases from 4.1 to 0.6 mmol/d. The total acid excretion has still not returned to the initial levels three days after treatment was halted, although the sulfate excretion returns to normal after 24 hours.

In the blood, however, the pH decreases only slightly in the first week by 0.05 pH units to pH 7.30, and in the second week recovers the initial level.

Standard bicarbonate (approx. 23.2 mmol/l) and $pCO_2$ (approx. 6.7 kPa) remain unchanged in the normal range, as do the ammonia levels in the serum. Thus, no tendency toward metabolic acidosis is found in the blood.

Electrolyte transformation

The sodium and potassium levels in the serum and the potassium and sodium excretion in the urine remain unchanged under cysteine-HCl loading. After the cysteine therapy stops, the potassium excretion levels decrease by 10 mmol/d.

Anion transformation

The chlorine excretion in the urine amounts to 24 mmol/d and thus is higher than corresponds to the greater input of 13.6 mmol/d. It remains still elevated during the three-day follow-up test. Normal chloride levels are found unaltered in the serum.

The excretion of sulfate in the urine increases under cysteine-HCl administration by 13.9 mmol/d average, which is almost the same as the additional sulfur input.

The serum sulfate levels increase slightly from 175 to 216 micromols per liter.

The bicarbonate excretion increases by 3.5 mmol/d average during the acidification.

The phosphate excretion increases by 5.5 mmol/d only during the first week of the administration of cysteine-HCl. In the average of the three weeks, this signifies an increase in the anion valences by about 2 mmol/d on account of the lessening of the valency of the phosphate ion in the acid.

In the serum no phosphate changes occur.

The excretion of citrate decreases from 2.81 to 1.82, which corresponds to an anion valence reduction at lowering pH levels of about 2 mmol/d. Even after the cysteine was discontinued, the citrate levels continued low for three days.

The excretion of uric acid and oxalate does not change during cysteine hydrochloride therapy, nor do the serum uric acid levels.

In all, with 41 mmol/d of acid treatment with cysteineHCl, about 48.5 mmol/d more of anion valences are eliminated by the kidneys; this contrasts with ain increased cation excretion of about 34 mmol/d (32 mmol $NH_4^+$, mmol $Ca^{++}$).

Mineral transformation and regulators

The excretion of calcium with the urine increases by 2.51 mmol/d from 4.68 to 7.19 mmol/d after cysteine-HCl treatment only in the first week of medication. Even after the fifth day and in the second week, the calcium excretion drops to the starting levels, so that these levels do not definitely change for 14 days.

No changes in the calcium level in the serum occur, either.

The excretion of magnesium is slightly increased, by 0.47 mmol/d, by cysteine-HCl treatment.

The parathyroid hormone level in the serum, in contrast to the $NH_4Cl$ acidoses, has a tendency to diminish under cysteine-HCl. Levels are found which are lower by about 39 ng/l than the initial level of 428 ng/l.

25-OH vitamin $D_3$ in the serum is reduced slightly by 7 nmol/l only in the first week of treatment, and in the second week returns to the initial levels, so that on the average no clear changes are to be observed throughout the period.

The cAMP excretion in the urine is not affected by cysteine-HCl. The values are around 5.2 micromols/d.

Kidney and liver function

The urine volume as well as the specific gravity remain constant over the entire experiment.

In the urine, the excretion of creatinine during the acid treatment is slightly higher at about 1.0 mmol/d, so that, with the serum creatinine unchanged, the creatinine clearance increases by 15 ml/min to 143 ml/min.

The gamma GT in the serum is around 10 units per liter throughout the experiment.

The acidosis under cysteine-HCl is a combined sulfate and HCl acidosis, since the SH groups of the cysteine are oxidized in the body cells through cysteinic acid to sulfate. The chlorine administered is not completely eliminated through the kidneys in the $NH_4Cl$ acidosis, but it is excreted in sulfate-HCl acidosis. In the serum, therefore, the sulfate level increases slightly.

The following Tables V and VI give the results obtained with different treatments with acid.

TABLE V

| | Changes produced in the serum parameters | | | | | | | | |
|---|---|---|---|---|---|---|---|---|---|
| | Group A 24 mmol HCl/d of acid mixture | | | Group B 48 mmol HCl/d of acid mixture | | | Group C 41 mmol $H^+$ as cysteine-HCl/d | | |
| Serum parameter | 1 wk | 2 wks | Tot. | 1 wk | 2 wks | Tot. | 1 wk | 2 wks | Tot. |
| pH | − | − | − | − | − | − | − | 0 | 0 |
| $HCO_3^-$ level | − | − | − | − | − | − | 0 | 0 | 0 |
| $pCO_2$ | + | + | + | 0 | 0 | 0 | 0 | 0 | 0 |
| $NH_4^+$ | − | − − | − | 0 | 0 | 0 | 0 | 0 | 0 |
| K | 0 | 0 | 0 | 0 | 0 | 0 | 0 | 0 | 0 |
| Na | 0 | 0 | 0 | 0 | 0 | 0 | 0 | 0 | 0 |
| $SO_4^-$ | | | | | | | ++ | + | + |
| Cl | 0 | 0 | 0 | 0 | 0 | 0 | 0 | 0 | 0 |
| Uric acid | − | − | − | 0 | + | + | 0 | 0 | 0 |
| $PO_4^-$ | 0 | + | + | 0 | + | + | 0 | (+) | 0 |
| Ca | − | 0 | − | (−) | − | − | 0 | 0 | 0 |
| Parathyroid hormone | (−) | ++ | + | − | + | 0 | 0 | − | − |
| 25-OH vit. $D_3$ | 0 | − | − | (−) | − | − | − | 0 | (−) |
| gamma-GT | 0 | − | 0 | − | − | − | 0 | 0 | 0 |
| K. clearance | + | + | + | + | (+) | + | + | + | + |
| creatinine | − | (−) | − | − | 0 | − | 0 | (−) | 0 |

The symbol 0 represents no change
+ represents significant increase
++ represents very significant increase
− represents significant reduction
− − represents very significant reduction, and
(+) and (−) represent an insignificant tendency in the positive or negative direction, respectively.

TABLE VI

| | Changes produced in the urine parameters | | | | | | | | |
|---|---|---|---|---|---|---|---|---|---|
| | Group A 24 mmol HCl/d of acid mixture | | | Group B 48 mmol HCl/d of acid mixture | | | Group C 41 mmol $H^+$ as cysteine-HCl/d | | |
| Urine parameter | 1 wk | 2 wks | Tot. | 1 wk | 2 wks | Tot. | 1 wk | 2 wks | Tot. |
| pH | − | − | − | − − | − − | − − | − − | − − | − − |
| $HCO_3^-$ | − | − | − | − | − | − | − | − | − |
| $pCO_2$ | − | − | − | − | − | − | − | − | − |
| $NH_4^+$ | + | + | + | ++ | ++ | ++ | + | + | + |
| Tit. acidity | (+) | + | + | ++ | ++ | ++ | + | + | + |
| Total acidity | + | + | + | ++ | ++ | ++ | + | + | + |
| K | 0 | 0 | 0 | − | − | − | 0 | 0 | 0 |
| Na | 0 | 0 | 0 | 0 | 0 | 0 | 0 | 0 | 0 |
| $SO_4^-$ | 0 | − | 0 | 0 | 0 | 0 | ++ | ++ | ++ |
| Cl | + | + | + | ++ | ++ | ++ | + | + | + |
| Uric acid | − | (−) | − | 0 | 0 | 0 | 0 | 0 | 0 |
| $PO_4^-$ | + | + | + | (+) | (+) | (+) | + | 0 | (+) |
| Ca | − | 0 | − | (−) | − | − | 0 | 0 | 0 |
| citrate | − | 0 | (−) | − | − − | − | − | − − | − |
| oxalate | (2) | 0 | 0 | 0 | 0 | 0 | (+) | 0 | 0 |
| Mg | 0 | 0 | 0 | 0 | 0 | 0 | + | + | + |
| Ca | + | ++ | + | + | ++ | + | + | 0 | (+) |
| cAMP | | | | | | | 0 | 0 | 0 |
| volume | 0 | 0 | 0 | + | 0 | 0 | 0 | 0 | 0 |
| sp. gr. | 0 | 0 | 0 | 0 | 0 | 0 | 0 | 0 | 0 |
| creatinine | (+) | (+) | (+) | 0 | 0 | 0 | + | + | + |

The symbol 0 represents no change
+ represents significant increase
++ represents very significant increase
− represents significant reduction
− − represents very significant reduction, and
(+) and (−) represent an insignificant upward or downward trend As it can be seen, under treatment with doses of mixed acids corresponding to 24 and 48 mmol $H^+$/d of acid mixture (one tablet=150 mg of $NH_4Cl$, 100 mg of lysine-HCl, 100 mg of betaine-HCl) which are much lower than those often used, there is a brief drop in the parathyroid hormone levels, followed by decided increases in the serum, which occur with a delay at higher doses. Hyperphosphaturia and hypercalciuria correlate with these increases, although in the serum a tendency toward a reduction of calcium and an increase of phosphate is to be observed. Also the lowering of 25-OH vitamin $D_3$ in the serum might be interpreted as an expression of a hyperparathyreotic metabolism situation, because the parathyroid hormone in the kidney activates 25-OH-1-alpha-hydroxylase, so that 25-OH vitamin $D_3$ has to diminish. The reduction of 25-OH vitamin $D_3$ also clearly correlates with a phosphaturic tendency. The inverse calcium-phosphate movement in the serum constitutes an additional stimulus to the secretion of the parathyroid hormone, which apparently becomes active more in the case of metabolic-acidotic metabolism.

The probably increased formation of $1.25\text{-}(OH)_2$ vitamin $D_3$ activates the absorption of calcium and phosphate in the gut and, together with parathyroid hormone, the resorption of bone, so that the calcium and phosphate losses occurring in the kidney under acidosis, which initially lead to decreases in the serum calcium, are so compensated that later on even a slight increase of phosphate in the serum results.

In the case of the greater acid input using 48 mmol of $H^+$ ions/d, the compensation of the calcium loss from the serum does not occur, because parathyroid hormone does not rise definitely until the end of the second week of treatment.

In the case of the cysteine-HCl dosage of 41 mmol of $H^+$ ions per day, which corresponds to a sulfate hydrochloride acidosis, increased parathyroid hormone secretion does not occur throughout the duration of the experiment, nor do any changes occur in the calcium and phosphate levels in the serum, although the urinary acidosis becomes visible and the serum sulfate levels are also slightly elevated. At the same time, however, the calcium and phosphate mobilization in the urine is also weaker, and no increase in the elimination of cAMP is to be observed in the urine. Only in the first week of the cysteine treatment is a slight reduction of the 25-OH vitamin $D_3$ levels in the serum observed, combined with a briefly elevated calcium and phosphate excretion in the urine. Despite slightly elevated serum sulfate levels, no changes in the blood gas analyses and other parameters of the mineral metabolism are detectable a few days after treatment with 41 mmol of $H^+$ ions/d, although the acidosis effect comes fully through in the urine. Here again, however, the calcium and phosphate excretion increases only at the beginning of the treatment over a period of about 5 days.

In all it can be stated that the use of cysteine as acid therapy is accompanied by much fewer side effects than the formerly common $NC_4Cl$ or L-methionine acidosis. L-cysteine is furthermore used in much smaller doses. 10 mmol of acid valence input results in a urine pH change by 0.15 pH units. The amounts to be administered should from then on be such that the pH of the urine remains definitely under 6.0 but does not drop below 5.0. Thus, cysteine-HCl daily doses of 2.25 g in the form of 3 tablets of 750 mg each are desirable.

L-cysteine has been used as a liver preparation in therapy for many years. Preparations containing 250 mg per tablet for daily doses up to one gram are known. At the present time there are numerous works which have to do with the protection of the liver, namely an action for the prevention and treatment of necrosis.

That L-cysteine-HCL.$H_2O$ has especially favorable properties as a means for the acidification of urine has long gone unrecognized.

It will be understood that the specification and examples are illustrative but not limitative of the present invention and that other embodiments within the spirit and scope of the invention will suggest themselves to those skilled in the art.

We claim:

1. A method of treating a nephro-urological disorder involving formation of phosphate renal calculi in urine comprising orally administering to a patient having a nephro-urological disorder characterized by formation of phosphate renal calculi in the urine an amount of L-cysteine or a pharmacologically acceptable acid addition salt of L-cysteine effective to acidify said urine to prevent formation of said phosphate renal calculi.

2. A method as in claim 1, wherein said disorder is characterized by the presence of phosphate kidney stones in said patient.

3. A method as in claim 1, wherein said disorder is characterized by an alkaline urine caused by urease.

4. A method as in claim 1, wherein said disorder is characterized by supersaturation of urine by phosphate salts.

5. A method as in claim 1, wherein said disorder is characterized by renal tubular acidosis.

6. A method as in claim 1, wherein said disorder is characterized by abnormal calcium or phosphate excretion.

7. A method of treating phosphate stone diathesis in a patient comprising orally administering to said patient an amount of L-cysteine or a pharmacologically acceptable acid addition salt thereof effective to acidify the urine of said patient so as to dissolve phosphate stones present in urine of said patient.

8. A method as in claim 1, wherein said L-cysteine acid addition salt is L-cysteine monohydrate monohydrochloride.

9. A method as in claim 8, wherein said salt is administered in amounts of about 0.75 g per dose.

10. A method as in claim 8, wherein said salt is administered in an amount of about 2.35 g per day.

11. A method as in claim 8, wherein said salt is administered to a patient for about two weeks.

12. A method as in claim 8, wherein said salt is administered before meals.

* * * * *